(12) United States Patent
Hsieh et al.

(10) Patent No.: US 9,243,185 B2
(45) Date of Patent: *Jan. 26, 2016

(54) POLYMERIZABLE MONOMER AND LIQUID CRYSTAL MATERIAL APPLIED TO DISPLAY PANEL

(71) Applicant: AU OPTRONICS CORP., Hsin-Chu (TW)

(72) Inventors: Chung-Ching Hsieh, Hsin-Chu (TW); Yang-Chu Lin, Hsin-Chu (TW); Hsi-Chien Lin, Hsin-Chu (TW); Te-Sheng Chen, Hsin-Chu (TW)

(73) Assignee: AU OPTRONICS CORP., Hsin-Chu (TW)

(*) Notice: Subject to any disclaimer, the term of this patent is extended or adjusted under 35 U.S.C. 154(b) by 55 days.

This patent is subject to a terminal disclaimer.

(21) Appl. No.: 14/068,979

(22) Filed: Oct. 31, 2013

(65) Prior Publication Data

US 2014/0065323 A1    Mar. 6, 2014

Related U.S. Application Data

(62) Division of application No. 12/787,105, filed on May 25, 2010, now Pat. No. 8,592,006.

(30) Foreign Application Priority Data

Oct. 2, 2009 (TW) .............................. 98133591 A

(51) Int. Cl.
| | |
|---|---|
| *C07C 69/94* | (2006.01) |
| *C09K 19/20* | (2006.01) |
| *C09K 19/30* | (2006.01) |
| *C09K 19/56* | (2006.01) |
| *C09K 19/12* | (2006.01) |
| *C09K 19/18* | (2006.01) |
| *C07C 69/618* | (2006.01) |

(Continued)

(52) U.S. Cl.
CPC .............. *C09K 19/56* (2013.01); *C07C 69/618* (2013.01); *C07C 69/736* (2013.01); *C07C 69/94* (2013.01);

(Continued)

(58) Field of Classification Search
CPC ....... C07C 69/94; C07C 69/618; C07C 69/78; C07C 69/653; C09K 19/08; C09K 19/12; C09K 19/18; C09K 19/2007; C09K 19/3003; C09K 19/32; C09K 19/322; C09K 19/56; C09K 2019/0407; C09K 2019/0411; C09K 2019/0448; C09K 2019/123; C09K 2019/301
See application file for complete search history.

(56) References Cited

U.S. PATENT DOCUMENTS

| 5,011,972 A | 4/1991 | Meier et al. |
| 6,013,197 A | 1/2000 | Parri et al. |

(Continued)

FOREIGN PATENT DOCUMENTS

| CN | 100334493 | 8/2007 |
| CN | 101418220 A | 4/2009 |

(Continued)

OTHER PUBLICATIONS

CAPLUS 2007: 1147800.*

*Primary Examiner* — Shean C Wu
(74) *Attorney, Agent, or Firm* — Rabin & Berdo, P.C.

(57) ABSTRACT

A polymerizable monomer adopted to a display panel is represented as following chemical formula:

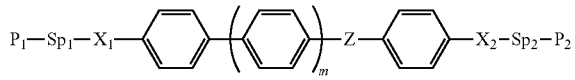

wherein, m≥0; "Z" is selected from oxygen, sulfur, carbonyl, caroboxyl, methyoxy, methylthio, thio, ethenylcarbonyl, carbonylethenyl, difluoromethoxy, difluoro methylthio, ethyl, difluoroethane, 1,2 difluoroethane, vinylene, difluoroethenylene, ethynyl, or single bond. "$X_1$" and "$X_2$" are independently selected from oxygen, sulfur, methyoxy, carbonyl, caroboxyl, -carbamoyl, methylthio, ethenylcarbonyl, carbonylethenyl, or single bond. "$Sp_1$" and "$Sp_2$" are independently a spacer or single bond. "$P_1$" and "$P_2$" are independently a polymerizable group.

13 Claims, 3 Drawing Sheets

(51) Int. Cl.
*C07C 69/736* (2006.01)
*C09K 19/08* (2006.01)
*C09K 19/04* (2006.01)

(52) U.S. Cl.
CPC ............... *C09K 19/08* (2013.01); *C09K 19/12* (2013.01); *C09K 19/18* (2013.01); *C09K 19/2007* (2013.01); *C09K 19/3003* (2013.01); *C09K 2019/0407* (2013.01); *C09K 2019/0448* (2013.01); *C09K 2019/123* (2013.01); *C09K 2019/301* (2013.01); *C09K 2219/03* (2013.01); *Y10T 428/10* (2015.01)

(56) References Cited

U.S. PATENT DOCUMENTS

| | | | |
|---|---|---|---|
| 6,117,920 A | 9/2000 | Jolliffe et al. | |
| 6,171,518 B1 | 1/2001 | Hikmet et al. | |
| 6,217,948 B1 | 4/2001 | Verrall et al. | |
| 6,316,066 B1 | 11/2001 | Jolliffe et al. | |
| 6,466,297 B1 | 10/2002 | Goulding et al. | |
| 6,544,605 B1 | 4/2003 | Verrall et al. | |
| 6,552,102 B2 | 4/2003 | Poetsch et al. | |
| 6,667,793 B2 | 12/2003 | Goulding et al. | |
| 6,677,042 B2 | 1/2004 | Kuntz et al. | |
| 7,083,834 B2 | 8/2006 | Kuntz et al. | |
| 7,731,865 B2 | 6/2010 | Bernatz et al. | |
| 7,820,072 B2 | 10/2010 | Hsieh et al. | |
| 7,993,710 B2 | 8/2011 | Hsieh et al. | |
| 8,592,006 B2 * | 11/2013 | Hsieh et al. | 428/1.1 |

FOREIGN PATENT DOCUMENTS

| | | | |
|---|---|---|---|
| JP | 04187487 A | * | 7/1992 |
| JP | 2004-123829 A | | 4/2004 |
| JP | 2007169363 A | * | 7/2007 |
| TW | 200838989 A | | 10/2008 |

* cited by examiner

| Liquid Crystal Material | | Ratio |
|---|---|---|
| The First Compound 1-2 | R—⬡—⬡—⌬(Cl)(F)—R' | 10.8% |
| The Second Compound 2-1 | R—⬡—⬡—R | 21.3% |
| The Second Compound 2-2 | R—⬡—⬡—⌬—R' | 5.8% |
| The Third Compound 3-1 | R—⬡—CH₂CH₂—⬡(F)(F)—R' | 25.7% |
| The Third Compound 3-2 | R—⬡—⌬—⌬(F)(F)—R' | 36.4% |
| Polymerizable Monomer H | (acrylate)—⌬—⌬—C≡C—⌬—(acrylate) | 0.1%~0.3% |

FIG. 1

|  | Conventional | The present embodiment |
|---|---|---|
| measured temperature (°C) | 25 | 25 |
| nematic-isotropic phase-transition temperature (Tni) (°C) | 79.4 | 79.5 |
| optical anisotropy (C25/M20°C, 589nm) An | 0.0909 | 0.0091 |
| optical anisotropy (C25/M20°C, 589nm) Ne | 1.5715 | 1.572 |
| optical anisotropy (C25/M20°C, 589nm) No | 1.4806 | 1.481 |
| dielectric anisotropy (25°C, 1KHz) Ae | -3.8 | -3 |
| dielectric anisotropy (25°C, 1KHz) e// | 3.5 | 3.3 |
| dielectric anisotropy (25°C, 1KHz) eL | 7.3 | 6.3 |
| rotational viscosity (mPa*s) $\gamma^1$ | 90 | 67 |
| elasticity constant (pN) (C25/M20°C) K11 | 15.8 | 14.2 |
| elasticity constant (pN) (C25/M20°C) K22 |  |  |
| elasticity constant (pN) (C25/M20°C) K33 | 15.1 | 14.6 |

FIG. 2

POLYMERIZABLE MONOMER AND LIQUID CRYSTAL MATERIAL APPLIED TO DISPLAY PANEL

This application is a divisional application of co-pending application Ser. No. 12/787,105, filed May 25, 2010, which claims the benefit of Taiwan application Serial No. 98133591, filed on Oct. 2, 2009, the subject matter of which is incorporated herein by reference.

BACKGROUND OF THE PRESENT INVENTION

1. Field of the Present Invention

The present invention relates in general to a polymerizable monomer and a liquid crystal material, and more particularly to a polymerizable monomer and a liquid crystal material adapted to a display panel.

2. Description of the Related Art

Liquid crystal display (LCD) panels, having the features of lightweight, thinness, low power consumption and low radiation, have been widely used in commercial and consumer electronic products, and has gradually replaced the conventional cathode ray tube (CRT) monitors. LCD panels are superior to the conventional cathode ray tube monitors in terms of power consumption, luminance and contrast, but are still slightly inferior to the conventional CRT monitors in terms of response time.

In recent years, a new alignment technology, that is, a polymer-stabilizing alignment (PSA) technology, is provided. According to the PSA technology, polymerizable monomers are mixed in a liquid crystal layer, and after the polymerizable monomers are arranged, an energy source (such as a UV light or a heating source) is applied thereto for polymerizing the polymerizable monomers into a polymer film, which guides the arrangement of the liquid crystal compounds in the LCD panel. Despite the PSA technology can conveniently form a polymer film facilitating the alignment of liquid crystal molecules, the performance of the polymer film in the alignment of liquid crystal molecules still needs to be improved.

SUMMARY OF THE PRESENT INVENTION

The present invention is directed to a polymerizable monomer which, when adapted to a liquid crystal material and a display panel, enhances the arrangement of liquid crystal molecules, shortens the manufacturing time, and at the same time enhances the alignment of liquid crystal molecules.

According to a first aspect of the present invention, a polymerizable monomer adapted to a display panel is provided. The polymerizable monomer is represented as the following chemical formula:

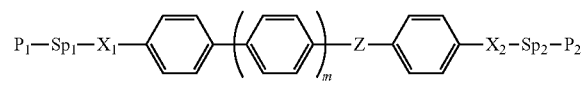

Wherein, m≥0;

"Z" is selected from oxygen, sulfur, carbonyl, caroboxyl, methyoxy, methylthio, thio, ethenylcarbonyl, carbonylethenyl, difluoromethoxy, difluoro methylthio, ethyl, difluoroethane, 1,2 difluoroethane, vinylene, difluoroethenylene, ethynyl, or single bond; "$X_1$" and "$X_2$" are independently selected from oxygen, sulfur, methyoxy, carbonyl, caroboxyl, carbamoyl, methylthio, ethenylcarbonyl, carbonylethenyl, or single bond;

"$Sp_1$" and "$Sp_2$" are independently a spacer or a single bond; and

"$P_1$" and "$P_2$" are independently a polymerizable group.

According to a second aspect of the present invention, a liquid crystal material adapted to a display panel is provided. The liquid crystal material includes a liquid crystal molecule and the said polymerizable monomer.

According to a third aspect of the present invention, a display panel is provided. The display panel includes a lower substrate, an upper substrate and a liquid crystal layer interposed between the two substrates. The liquid crystal layer includes the said liquid crystal material.

The present invention will become apparent from the following detailed description of the preferred but non-limiting embodiments. The following description is made with reference to the accompanying drawings.

BRIEF DESCRIPTION OF THE DRAWINGS

FIG. 1 shows the composition and the ratios of a liquid crystal material according to a preferred embodiment of the present invention;

FIG. 2 shows a comparison of characteristics between a conventional liquid crystal material and the liquid crystal material according to a preferred embodiment of the present invention;

DETAILED DESCRIPTION OF THE PRESENT INVENTION

Figure 3:
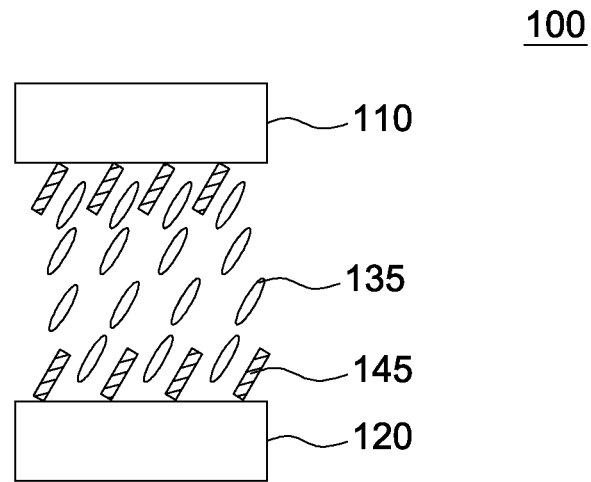
FIG. 3 shows a side view of a display panel according to a preferred embodiment of the present invention.

The present invention mainly provides a polymerizable monomer which, when adapted to a liquid crystal material and a display panel, enhances the arrangement of liquid crystal molecules, shortens the manufacturing time, and at the same time enhances the alignment of liquid crystal molecules. The chemical formula, preferred embodiments and synthesis of the polymerizable monomer are disclosed and followed by the features and advantages of the liquid crystal material and the display panel using the same.

Polymerizable Monomer

The present invention mainly provides a polymerizable monomer, whose hard core structure has a tiny dihedral angle or can even be a coplanar structure. The polymerizable monomer has excellent performance in the arrangement of liquid crystal molecules. Furthermore, since the UV light dose required for polymerization is reduced, the manufacturing time is shorted, and energy consumption is reduced. After the polymerizable monomer is polymerized into a polymer film, the polymer film also has excellent performance in the alignment of liquid crystal molecules. The polymerizable monomer of the present invention is represented as the following chemical formula:

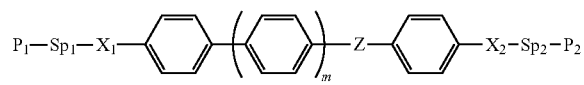

Wherein, $m \geq 0$:

"Z" is selected from oxygen, sulfur, carbonyl (—C=O—), caroboxyl (—COO—, —OCO—), methoxy (—OCH$_2$—), methylthio (—CH$_2$S—, —SCH$_2$—), thio (—H$_2$S—, —SH$_2$—), ethenylcarbonyl (—CH=CH—COO—), carbonylethenyl (—OOC—CH=CH—), difluoromethoxy (—CF$_2$O—, —OCF$_2$—), difluoro methylthio (—CF$_2$S—, —SCF$_2$—), ethyl (—C$_2$H$_4$—), difluoroethane (—CF$_2$CH$_2$—, —CH$_2$CF$_2$—), 1,2 difluoroethane (—CF$_2$CF$_2$—), vinylene (—CH=CH—), difluoroethenylene (—CF=CF—), ethynyl (—C≡C—), or single bond.

"X$_1$" and "X$_2$" are independently selected from oxygen, sulfur, methoxy (—OCH$_2$—), carbonyl (—C=O—), caroboxyl (—COO—, —OCO—), -carbamoyl (—CO—N$^0$R—, —N$^0$R—CO—), methylthio (—SCH$_2$—, —CH$_2$S—), ethenylcarbonyl (—CH=CH—COO—), carbonylethenyl (—OOC—CH=CH—), or single bond.

"Sp$_1$" and "Sp$_2$" are independently a spacer or a single bond.

"P$_1$" and "P$_2$" are independently a polymerizable group; "P$_1$" and "P$_2$" can be selected from group I, II, III, IV, or V;

Group I is represented as the following chemical formula:

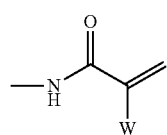

[I]

"W" is selected from hydrogen, methyl, fluorine, trifluoromethyl (—CF$_3$), and phenyl.

Group II is represented as the following chemical formula:

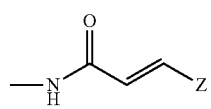

[II]

"Z" is selected from hydrogen, methyl, fluorine, trifluoromethyl, and phenyl.

Group III is represented as the following chemical formula:

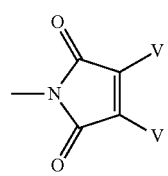

[III]

"V" is selected from hydrogen or methyl.

Group IV is represented as the following chemical formula:

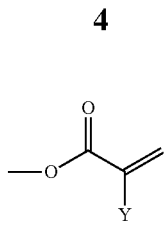

[IV]

"Y" is selected from hydrogen, methyl, fluorine, trifluoromethyl, and phenyl.

Group V is represented as the following chemical formula:

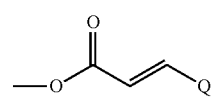

[V]

"Q" is selected from methyl, fluorine, trifluoromethyl, and phenyl.

A number of embodiments are exemplified below for more detailed description of the polymerizable monomer and the synthesis thereof. In the light of structure, all of the compounds (that is, the compounds A~I) exemplified in the following embodiments have a hard core structure having a tiny dihedral angle or being even a coplanar structure, and thus have excellent performance in the arrangement and alignment of liquid crystal molecules. Despite the UV light absorption wavelengths of the compounds in the first and the second embodiment (that is, the compounds A and B) are substantially smaller than 300 nm, the UV light doses for perfect polymerization required by the compounds in the first and the second embodiment are less than that required by the conventional monomer, not only saving manufacturing cost but also producing preferred alignment effect. The UV light absorption wavelengths of the polymerizable monomer in the third to the ninth embodiment (that is, the compounds C~I) are substantially larger than 300 nm, and the UV light doses for perfect polymerization required by the compounds in the third to the eighth embodiment are even less than that required by the compounds in the first and the second embodiment, further saving manufacturing cost and achieving preferred alignment effect. However, anyone who is skilled in the technology of the technology of the present invention will understand that the polymerizable monomer of the present invention is not limited to the compounds disclosed above, and various adjustments and modifications can be made as long as the spirit and scope of the present invention are accorded.

First Embodiment

Each substituent in the chemical formula of the said polymerizable monomer is substituted as follows: m=0, "Z" is a caroboxyl, "X$_1$", "X$_2$", "Sp$_1$", and "Sp$_2$" respectively are a single bond, "P$_1$" and "P$_2$" respectively are a group IV, that is, the compound A. "Y" (that is, "R" in the diagram) of group IV is hydrogen, methyl, fluorine atom, trifluoromethyl, and phenyl.

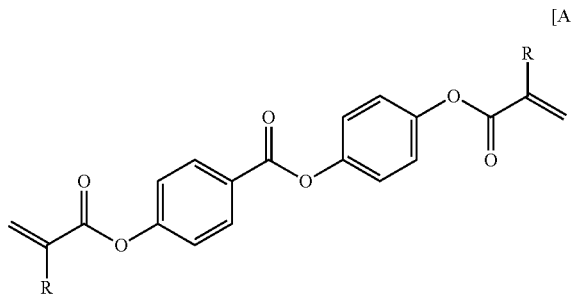

[A]

In the light of structure, the dihedral angle of the hard core structure of the compound A is tiny and the UV light absorption wavelength of the compound A is substantially smaller than 300 nm. On the other hand, the synthesis of polymerizable monomer of the present embodiment is represented by the following chemical reaction scheme:

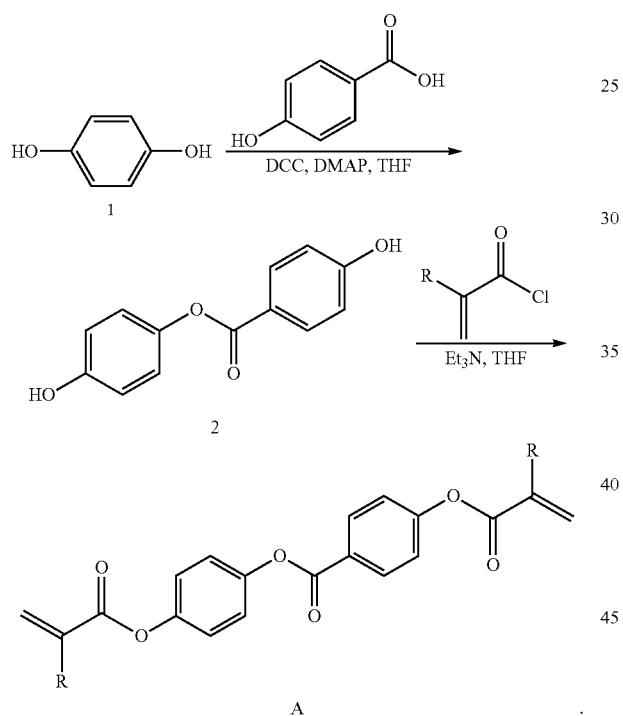

About 4 milli-mole (mmol) of hydroquinone, about 1 mmol of 4-hydroxybenzoic acid, and about 0.1 mmol of 4-dimethylaminopyridine (DMAP) and about 50 ml of dehydrated tetrahydrofuran (THF) are loaded into a about 250 ml two-neck bottle which is then deaerated with a vacuum dehydrating and deaerating device and nitrogenated for three times. Next, nitrogen is connected to the drip tube for making the reaction system anaerobic and anhydrous. Then, under freezing condition, about 1.1 mmol of dicyclohexylcarbodiimide (DCC) are added to the reaction system which reacts until the next day at the room temperature. The reaction system is suction filtrated with THF. The collected filtrate is decompressed and evaporated, extracted with ethyl acetate (EA) and water, dehydrated with magnesium sulfate ($MgSO_4$), suction filtrated and evaporated and vacuumed to obtain a yellow solid. Lastly, the yellow solid is purified with EA/hexane (EA/hexane=2/8) through silica gel column chromatography to obtain a yellow solid which is further crystallized with THF/methanol to obtain a product 2.

About 4.14 mmol of product 2 are loaded into a about 250 ml two-neck bottle which is then deaerated with a vacuum dehydrating and deaerating device and nitrogenated for three times. Next, nitrogen is connected to the drip tube for making the reaction system anaerobic and anhydrous. At the room temperature, about 8.28 mmol of triethylamine ($Et_3N$) and about 50 ml dehydrated THF are added to the reaction system and are stirred until dissolved. Then, under freezing condition, about 9.11 mmol of methacryloyl chloride are added to the reaction system which reacts until the next day at the room temperature. The reaction system is suction filtrated with THF, and the filtrate is collected, decompressed and evaporated, extracted with EA and water, dehydrated with magnesium sulfate ($MgSO_4$), suction filtrated and evaporated and vacuumed to obtain a yellow solid. Lastly, the yellow solid is purified with EA/hexane (EA/hexane=1/6) through silica gel column chromatography to obtain a yellowish solid which is further crystallized with THF/methanol to obtain a polymerizable monomer of the present embodiment of the present invention, that is, the compound A.

Second Embodiment

Each substituent in the chemical formula of the said polymerizable monomer is substituted as follows: m=1, "Z" is a caroboxyl, "$X_1$", "$X_2$", "$Sp_1$", and "$Sp_2$" respectively are a single bond, "$P_1$" and "$P_2$" respectively are a group IV, that is, the compound B. "Y" (that is, "R" in the diagram) of group IV is:

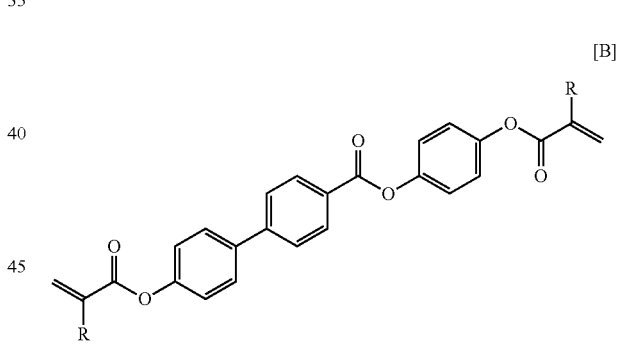

[B]

In the light of structure, the dihedral angle of the hard core structure of the compound B is tiny and the UV light absorption wavelength of the compound B is substantially smaller than 300 nm. On the other hand, the synthesis of polymerizable monomer of the present embodiment is represented by the following chemical reaction scheme:

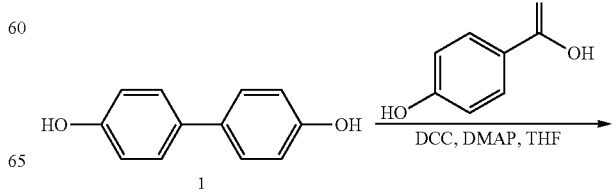

-continued

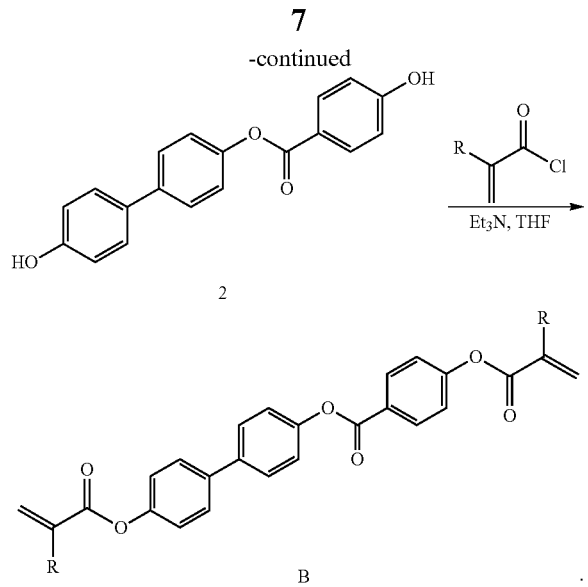

About 4 mmol of 4,4'-dihydroxybiphenyl about 1 mmol of 4-hydroxybenzoic acid and about 0.1 mmol of DMAP and about 50 ml of dehydrated tetrahydrofuran (THF) are loaded into a about 250 ml two-neck bottle which is then deaerated with a vacuum dehydrating and deaerating device and nitrogenated for three times. Next, nitrogen is connected to the drip tube for making the reaction system anaerobic and anhydrous. Then, under freezing condition, about 1.1 mmol of dicyclohexylcarbodiimide (DCC) are added to the reaction system which reacts until the next day at the room temperature. The reaction system is suction filtrated with THF, and the filtrate is collected, decompressed and evaporated, extracted with EA and water, dehydrated with MgSO$_4$, suction filtrated and evaporated and vacuumed to obtain a yellow solid. Lastly, the yellow solid is purified with EA/hexane (EA/hexane=2/8) through silica gel column chromatography to obtain a yellow solid which is further crystallized with THF/methanol to obtain a product 2.

About 4.14 mmol of product 2 are loaded into a about 250 ml two-neck bottle which is then deaerated with a vacuum dehydrating and deaerating device and nitrogenated for three times. Next, nitrogen is connected to the drip tube for making the reaction system anaerobic and anhydrous. At the room temperature, about 8.28 mmol of triethylamine (Et$_3$N) and about 50 ml of dehydrated THF are added to the reaction system and are stirred until dissolved. Then, under freezing condition, about 9.11 mmol of methacryloyl chloride are added to the reaction system which reacts until the next day at the room temperature. The reaction system is suction filtrated with THF, and the filtrate is collected, decompressed and evaporated, extracted with EA and water, dehydrated with magnesium sulfate (MgSO$_4$), suction filtrated and evaporated and vacuumed to obtain a yellow solid. Lastly, the yellow solid is purified with EA/hexane (EA/hexane=1/6) through silica gel column chromatography to obtain a yellowish solid which is further crystallized with THF/methanol to obtain a polymerizable monomer of the present embodiment, that is, the compound B.

Third Embodiment

Each substituent in the chemical formula of the said polymerizable monomer is substituted as follows: m=0, "Z", "X$_1$", "X$_2$", "Sp$_1$", and "Sp$_2$" respectively are a single bond, "P$_1$" and "P$_2$" respectively are a group IV, that is, the compound C. "Y" (that is, "R" in the diagram) of group IV is a hydrogen atom, methyl, fluorine atom, trifluoromethyl, and phenyl.

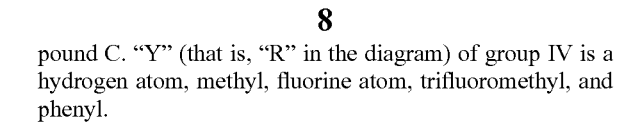

In the light of structure, the dihedral angle of the hard core structure of the compound C is tiny and the UV light absorption wavelength of the compound C is substantially smaller than 300 nm. In the present embodiment of the present invention, the synthesis of polymerizable monomer is represented by the following chemical reaction scheme:

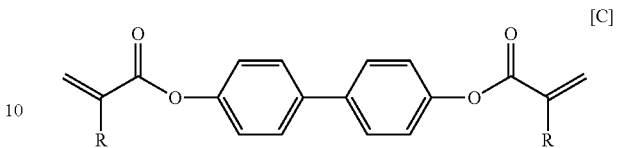

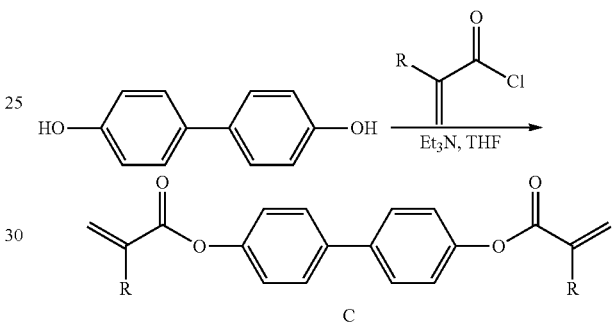

About 4.14 mmol of 4,4'-dihydroxybiphenyl are loaded into a about 250 ml two-neck bottle which is then deaerated with a vacuum dehydrating and deaerating device and nitrogenated for three times. Next, nitrogen is connected to the drip tube for making the reaction system anaerobic and anhydrous. At the room temperature, about 8.28 mmol of triethylamine (Et$_3$N) and about 50 ml dehydrated tetrahydrofuran (THF) are added into the reaction system and are stirred until dissolved. Then, under freezing condition, about 9.11 mmol of methacryloyl chloride are added to the reaction system which reacts until the next day at the room temperature. The reaction system is suction filtrated with THF, and the filtrate is collected, decompressed and evaporated, extracted with EA and water, dehydrated with MgSO$_4$, suction filtrated and evaporated and vacuumed to obtain a yellow solid. Lastly, the yellow solid is purified with EA/hexane=1/6 through silica gel column chromatography to obtain a yellowish solid which is further crystallized with THF/methanol to obtain a polymerizable monomer of the present embodiment, that is, the compound C.

Fourth Embodiment

Each substituent in the chemical formula of the said polymerizable monomer is substituted as follows: m=0, "Z" is an ethynyl, "X$_1$", "X$_2$", "Sp$_1$", and "Sp$_2$" respectively are a single bond, "P$_1$" and "P$_2$" respectively are a group IV, that is, the compound D. "Y" (that is, "R" in the diagram) of group IV is a hydrogen atom, methyl, fluorine atom, trifluoromethyl, and phenyl.

[D]

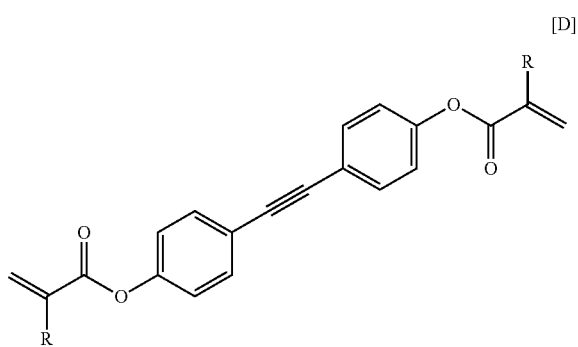

In the light of structure, the dihedral angle of the hard core structure of the compound D is tiny and can even be coplanar so as to have better performance in alignment. Besides, the UV light absorption wavelength of the compound D is substantially larger than 300 nm so as to shorten the required radiation time for perfect polymerization. In the present embodiment of the present invention, the synthesis of polymerizable monomer is represented by the following chemical reaction scheme:

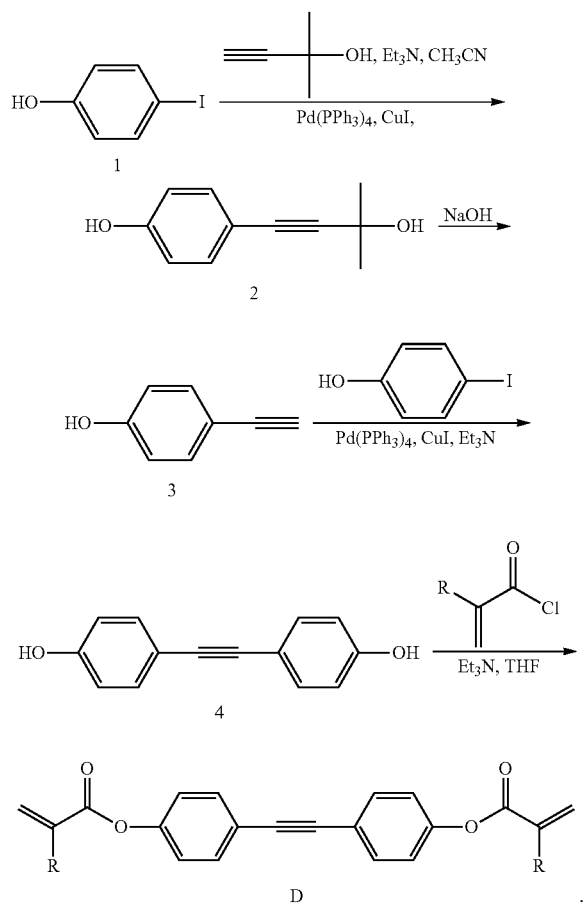

Under nitrogen environment, the reactant 1 is dissolved in a mixed solution of $CH_3CN$, triethylamine ($Et_3N$), tetrakistriphenylphosphine palladium ($Pd(PPh_3)_4$) and copper iodide (CuI) and then heated to about 70. 3-methyl-1-butyne-3-ol is continually added to the mixed solution drop by drop for 1 hour, and the mixed solution is then stirred for about 2 hours at the room temperature, 1 hour at about 50, 30 minutes at about 60 and 2 hours at about 80. After that, the mixed solution is hydrated and cooled to the room temperature, and then a concentrated hydrochloric acid solution is further added to the mixed solution. After the mixed solution is extracted with ethyl acetate (EA) twice, the extracts mixed in an organic layer are sequentially washed with water solution and a saturated saline solution. Then, the extracts are dehydrated with anhydrous magnesium sulfate ($MgSO_4$). After the solvent is evaporated through decompression, column chromatography (silica gel column, methylbenzene) is performed on the residuals to obtain a product 2.

Sodium hydroxide is added to the product 2 and then the mixture is then stirred for 1 hour at about 120, wherein the generated acetone is removed by using a pressure evaporator. After that, the product 2 is purified by column chromatography (silica gel column, methylbenzene) to obtain a product 3.

Under nitrogen environment, iodophenol is dissolved in a mixed solution of dimethylformamide (DMF), triethylamine ($Et_3N$), tetrakistriphenylphosphine palladium ($Pd(PPh_3)_4$) and copper iodide (CuI), and the mixed solution is heated to about 55. The product 3 is continually added to the mixed solution drop by drop for 20 minutes, and then the mixed solution is stirred for 3 hours. After that, the mixed solution is hydrated and cooled to the room temperature, and then a concentrated hydrochloric acid solution is further added to the mixed solution. After the mixed solution is extracted with ethyl acetate (EA) twice, the extracts mixed in an organic layer are sequentially washed with water solution and a saturated saline solution. Then, the extracts are dehydrated with anhydrous magnesium sulfate ($MgSO_4$). After the solvent is evaporated through decompression, column chromatography (silica gel column, methylbenzene) is performed on the residuals to obtain a product 4.

About 4.14 mmol of product 4 are loaded into a about 250 ml two-neck bottle which is then deaerated with a vacuum dehydrating and deaerating device and nitrogenated for three times. Next, nitrogen is connected to the drip tube for making the reaction system anaerobic and anhydrous. At the room temperature, about 8.28 mmol of triethylamine ($Et_3N$) and about 50 ml of dehydrated THF are added to the reaction system and are stirred until dissolved. Then, under freezing condition, about 9.11 mmol of methacryloyl chloride are added to the reaction system which reacts until the next day at the room temperature. The reaction system is suction filtrated with THF, and the filtrate is collected, decompressed and evaporated, extracted with EA and water, dehydrated with $MgSO_4$, suction filtrated and evaporated and vacuumed to obtain a yellow solid. Lastly, the yellow solid is purified with EA/hexane=1/6 through silica gel column chromatography to obtain a yellowish solid which can also be crystallized with THF/methanol to obtain a polymerizable monomer of the present embodiment, that is, the compound D.

Fifth Embodiment

Each substituent in the chemical formula of the said polymerizable monomer is substituted as follows: m=0, "Z" is an ethynyl, "$X_1$" and "$X_2$" respectively are an oxygen atom, "$Sp_1$" and "$Sp_2$" respectively are an ethyl, "$P_1$" and "$P_2$" respectively are group IV, that is, the compound E. "Y" (that is, "R" in the diagram) of group IV is a hydrogen atom, methyl, fluorine atom, trifluoromethyl, and phenyl.

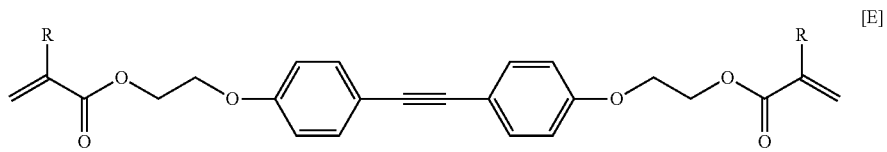

In the light of structure, the dihedral angle of the hard core structure of the compound E is tiny and even can be coplanar so as to have better performance in alignment. Besides, the UV light absorption wavelength of the compound E is substantially larger than 300 nm so as to shorten the required radiation time for perfect polymerization. In the present embodiment of the present invention, the synthesis of polymerizable monomer is represented by the following chemical reaction scheme:

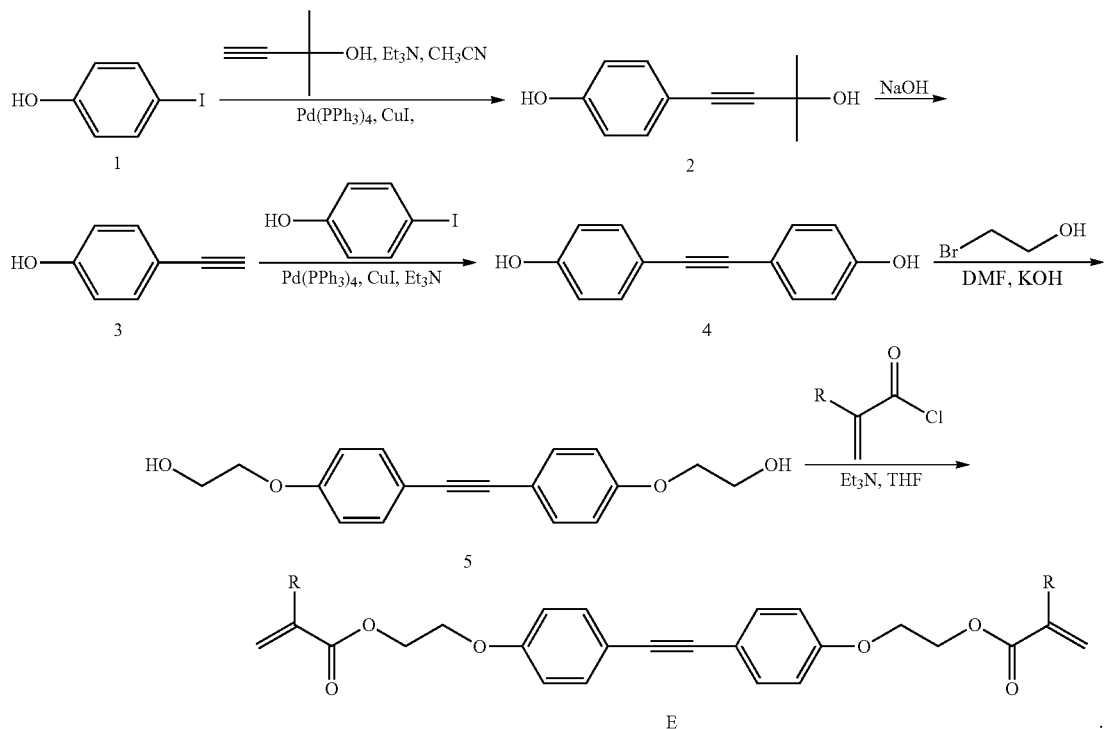

The product 4 is obtained from the reactant 1 according to the method disclosed in the fourth embodiment. Under nitrogen environment, the product 4 is dissolved in a mixed solution of DMF and potassium hydroxide solution, and the mixed solution is then heated to reflow. 2-bromoethenol is continually added to the mixed solution drop by drop for 20 minutes, and then the mixed solution is stirred for 12 hours. Next, the mixed solution is hydrated and cooled to the room temperature, and then a concentrated hydrochloric acid solution is further added to the mixed solution. After the mixed solution is extracted with ethyl acetate (EA) twice, the extracts mixed in an organic layer are sequentially washed with water solution and a saturated saline solution. Then, the extracts are dehydrated with anhydrous magnesium sulfate ($MgSO_4$). After the solvent is evaporated through decompression, column chromatography (silica gel column, methylbenzene) is performed on the residuals to obtain a product 5.

About 4.14 mmol of product 5 are loaded into a about 250 ml two-neck bottle which is then deaerated with a vacuum dehydrating and deaerating device and nitrogenated for three times. Next, nitrogen is connected to the drip tube for making the reaction system anaerobic and anhydrous. At the room temperature, $Et_3N$ (about 8.28 mmol) and about 50 ml of dehydrated THF are added to the reaction system which is then stirred until dissolved. Then, under freezing condition, mathacryloyl chloride (about 9.11 mmol) is added to the reaction system which reacts until the next day at the room temperature. The reaction system is suction filtrated with THF, and the filtrate is collected, decompressed and evaporated, extracted with EA and water, dehydrated with $MgSO_4$, suction filtrated and evaporated and vacuumed to obtain a yellow solid. Lastly, the yellow solid is purified with EA/hexane=1/6 through silica gel column chromatography to obtain a yellowish solid which can also be crystallized with THF/methanol to obtain a polymerizable monomer of the present embodiment, that is, the compound E.

Sixth Embodiment

Each substituent in the chemical formula of the said polymerizable monomer is substituted as follows: m=1, "Z" is a single bond, "$X_1$", "$X_2$", "$Sp_1$", and "$Sp_2$" respectively are a single bond, "$P_1$" and "$P_2$" respectively are a group IV, that is, the compound F. "Y" (that is, "R" in the diagram) of group IV is a hydrogen atom, methyl, fluorine atom, trifluoromethyl, and phenyl.

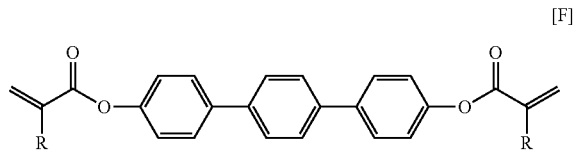

In the light of structure, the dihedral angle of the hard core structure of the compound F is tiny, and the UV light absorption wavelength of the compound F is substantially larger than 300 nm. In the present embodiment of the present invention, the synthesis of polymerizable monomer is represented by the following chemical reaction scheme:

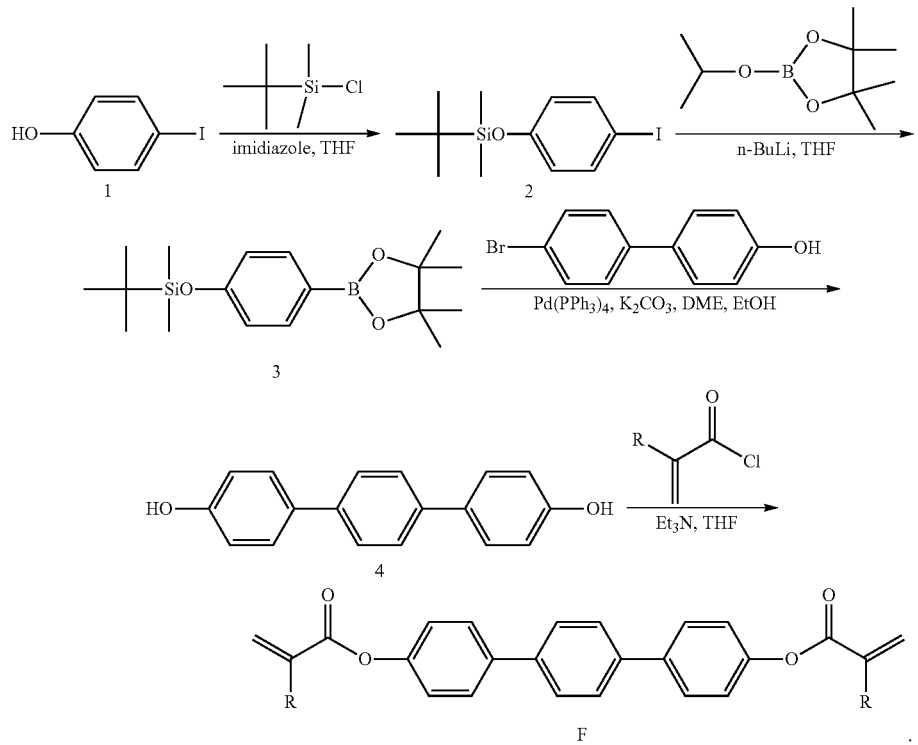

About 10 grams (about 0.045 mol) of iodophenol, about 9.6 grams (about 0.064 mol) of tert-Butyldimethylsilyl chloride and about 9.3 grams (about 0.204 mol) of imidiazole are loaded into a about 250 ml two-neck bottle. Then, about 60 ml of dehydrated THF are added to the reaction system which is then stirred for 6 hours. After the reaction system is suction filtrated and most of the solvent is removed by using a rotary evaporator, the reaction system is extracted with EA and a saturated saline solution. Then, the collected filtrate is dehydrated with anhydrous magnesium sulfate, decompressed and evaporated to obtain a light orange liquid. Then, column chromatography separation is performed on the light orange liquid which is purified with a perfusion stream realized by hexane to obtain an orange liquid, that is, the product 2. The yield rate is about 87%. $^1$H-NMR (CDCl$_3$, ppm): δ=0.20 (s, 6H, (CH$_3$)$_3$CSiO(CH$_3$)$_2$—), δ=0.99 (s, 9H, (CH$_3$)$_3$ CSiO (CH$_3$)$_2$—), δ=6.61~6.64 (d, 2H, aromatic protons), δ=7.50~7.53 (d, 2H, aromatic protons) IR (film) V$_{max}$/cm$^{-1}$ 662, 1220, 1225, 1256, 2928, 2934.

10 grams of the product 2 (about 29.92 mmol) having been vacuumed and dried are added to a about 250 ml two-neck bottle which has been vacuumed and dried by heating. Dried THF is sucked by a syringe and is then infused into the reaction bottle and stirred for 5 minutes at about −78. Then, about 1.6 M n-butyllithium (30 Ml are about 44.87 mmol) are slowly dropped into the reaction bottle and stirred for 2 hours at about −78. Meanwhile, the clear solution will turn into a white cloudy solution. After that, 2-isopropoxy-4,4,5,5-tetramethyl-1,3,2-dioxaborolane (about 15 ml are about 59.83 mmol), slowly dropped into the reaction bottle at about −78 environment, gradually returns to the room temperature and reacts overnight. After the reaction is completed, the white solid is suction filtrated. After the filtrate is decompressed and evaporated, the filtrate is extracted with water and EA. An organic layer is collected, and then is dehydrated and evaporated with anhydrous magnesium sulfate to obtain a yellowish liquid. The yellowish liquid is further purified with perfusion stream realized by EA/hexane=1/10 through column chromatography to obtain a yellowish solid, that is, the product 3. The yield rate is about 77%, and the melting point substantially ranges between 45~46° C. $^1$H-NMR (CDCl$_3$, ppm): δ=0.18 (s, 6H, (CH$_3$)$_3$CSiO(CH$_3$)$_2$—), δ=0.97 (s, 9H, (CH$_3$)$_3$ CSiO (CH$_3$)$_2$—), δ=1.30 (s, 12H, —BOC(CH$_3$)$_2$—), δ=6.81~6.84 (d, 2H, aromatic protons), δ=7.68~7.71 (d, 2H, aromatic protons) IR (film) V$_{max}$/cm$^{-1}$ 1014, 1090, 1214, 1262, 1262, 1264, 1360, 2930, 2957, 2978.

The product 3 (about 5 grams are about 15 mmol), 4'-boromo-(1,1'-biphenyl)-4-o (about 14 mmol) and K$_2$CO$_3$ (about 15.48 g about 112 mmol) is loaded into a about 50 ml two-neck bottle. Pd(PPh$_3$)$_4$ (about 0.81 g is about 0.7 mmol), taken from a glove box, is loaded into a reaction bottle and then the reaction bottle is wrapped with an aluminum foil. A mixed solution of vacuum dried 1,2-Dimethoxyethane/ EtOH=3:1 is added to the reaction bottle, and then the reaction system is reflown and heated for one day at about 90° C. After the reaction is completed, the mixed solution is extracted with EA and saturated NH₄Cl, and an organic layer is collected. Then the extracts are dehydrated and evaporated with anhydrous magnesium sulfate. Lastly, the extracts are purified with EA/hexane=1/6 through silica gel column chromatography to obtain a white solid, that is, the product 4. The yield rate is about 65%.

The product 4 (about 4.14 mmol) is loaded into a about 250 ml two-neck bottle which is then deaerated with a vacuum dehydrating and deaerating device and nitrogenated for three times. Next, nitrogen is connected to the drip tube for making the reaction system anaerobic and anhydrous. At the room temperature, Et₃N (about 8.28 mmol) and about 50 ml of dehydrated THF are added to the reaction system which is then stirred until dissolved. Then, under freezing condition, mathacryloyl chloride (about 9.11 mmol) is added to the reaction system which reacts until the next day at the room temperature. The reaction system is suction filtrated with THF, and the filtrate is collected, decompressed and evaporated, extracted with EA and water, dehydrated with MgSO₄, suction filtrated and evaporated and vacuumed to obtain a yellow solid. Lastly, the yellow solid is purified with EA/hexane=1/6 through silica gel column chromatography to obtain a yellowish solid which can also be crystallized with THF/methanol. Lastly, a polymerizable monomer of the present embodiment of the present invention, that is, the compound F, is obtained.

Seventh Embodiment

Each substituent in the chemical formula of the said polymerizable monomer is substituted as follows: m=1, "Z" is a single bond, "$X_1$" and "$X_2$" respectively are an oxygen atom, "$Sp_1$" and "$Sp_2$" respectively are an ethyl, "$P_1$" and "$P_2$" respectively are group IV, that is, the compound G. "Y" (that is, "R" in the diagram) of group IV is a hydrogen atom, methyl, fluorine atom, trifluoromethyl and phenyl.

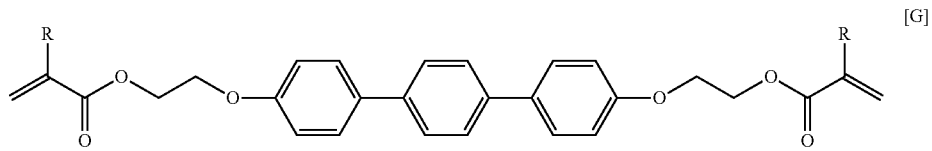

[G]

In the light of structure, the dihedral angle of the hard core structure of the compound G is tiny, and the UV light absorption wavelength of the compound G is substantially larger than 300 nm. In the present embodiment of the present invention, the synthesis of polymerizable monomer is represented by the following chemical reaction scheme:

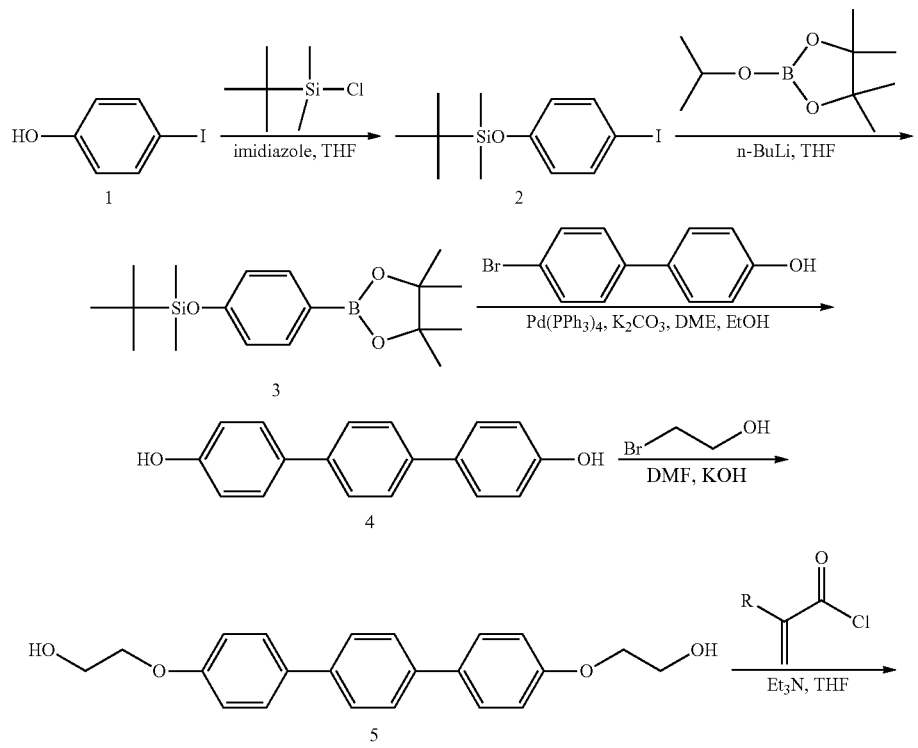

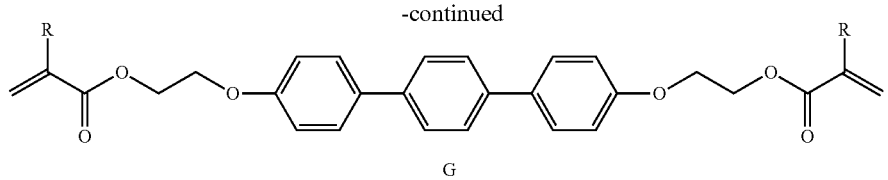

G

The product 4 is obtained from the reactant 1 according to the method of the sixth embodiment. Under nitrogen environment, the product 4 is dissolved in a mixed solution of DMF and potassium hydroxide and the mixed solution is then heated to reflow. 2-bromoethenol is continually added to the mixed solution drop by drop for 20 minutes, and then the mixed solution is stirred for 12 hours. Next, the mixed solution is hydrated and cooled to the room temperature, and then a concentrated hydrochloric acid solution is further added to the mixed solution. After the mixed solution is extracted with ethyl acetate (EA) twice, the extracts mixed in an organic layer are sequentially washed with water solution and a saturated saline solution, and then are dehydrated with anhydrous magnesium sulfate ($MgSO_4$). After the solvent is evaporated through decompression, column chromatography (silica gel column, methylbenzene) is performed on the residuals to obtain a product 5.

The product 5 (about 4.14 mmol) is loaded into a about 250 ml two-neck bottle, which is then deaerated with a vacuum dehydrating and deaerating device and nitrogenated for three times. Next, nitrogen is connected to the drip tube for making the reaction system anaerobic and anhydrous. At the room temperature, $Et_3N$ (about 8.28 mmol) and about 50 ml of dehydrated THF are added to the reaction system which is then stirred until dissolved. Then, under freezing condition, mathacryloyl chloride (about 9.11 mmol) is added to the reaction system which reacts until the next day at the room temperature. The reaction system is suction filtrated with THF, and the filtrate is collected, decompressed and evaporated, extracted with EA and water, dehydrated with $MgSO_4$, suction filtrated and evaporated and vacuumed to obtain a yellow solid. Lastly, the yellow solid is purified with EA/hexane=1/6 through silica gel column chromatography to obtain a yellowish solid which can also be crystallized with THF/methanol. Lastly, a polymerizable monomer of the present embodiment of the present invention, that is, the compound G, is obtained.

Eighth Embodiment

Each substituent in the chemical formula of the said polymerizable monomer is substituted as follows: m=1, "Z" is an ethynyl, "$X_1$", "$X_2$", "$Sp_1$", and "$Sp_2$" respectively are a single bond, "$P_1$" and "$P_2$" respectively are a group IV, that is, the compound H. "Y" (that is, "R" in the diagram) of group IV is a hydrogen atom, methyl, fluorine atom, trifluoromethyl, and phenyl.

[H]

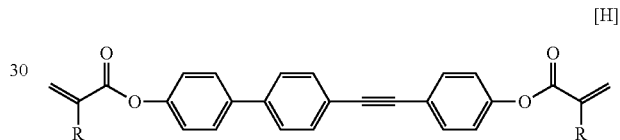

In the light of structure, the dihedral angle of the hard core structure of the compound H is tiny and the structure can even be coplanar so as to have better performance in alignment. Beside, the UV light absorption wavelength of the compound H is substantially larger than 300 nm so as to shorten the required radiation time for perfect polymerization. In the present embodiment, the synthesis of polymerizable monomer is represented by the following chemical reaction scheme:

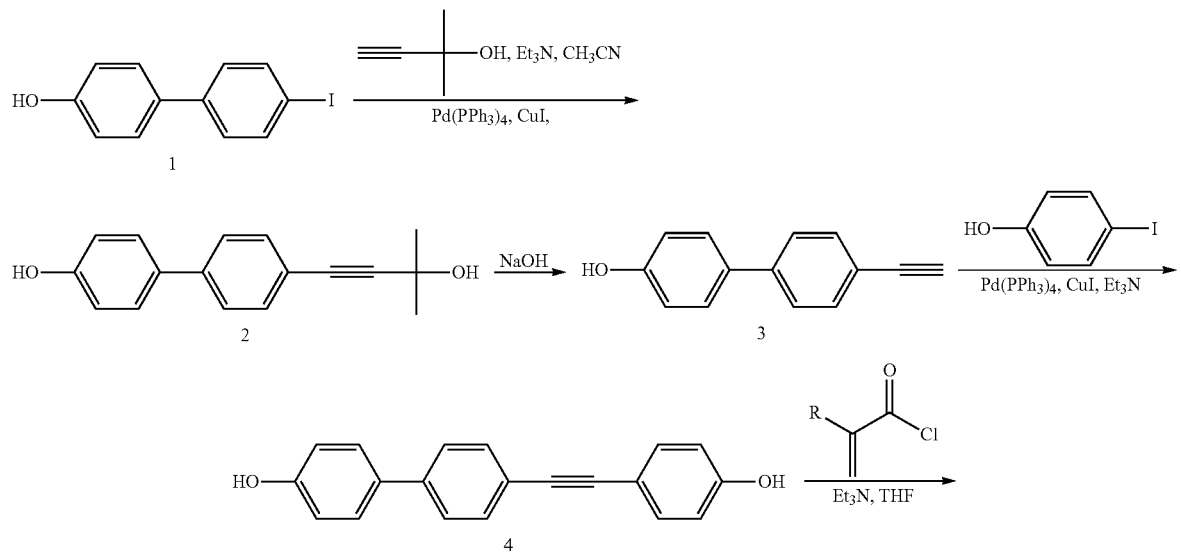

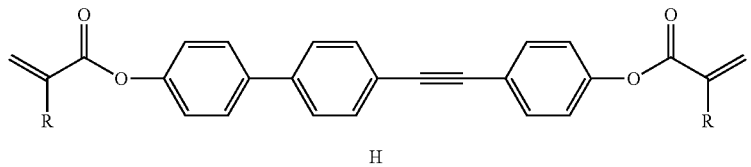

H

Under nitrogen environment, the reactant 1 is dissolved in a mixed solution of $CH_3CN$, triethylamine ($Et_3N$), tetrakistriphenylphosphine palladium ($Pd(PPh_3)_4$) and copper iodide (CuI), and the mixed solution is then heated to 70. 3-methyl-1-butyne-3-ol is continually added to the mixed solution drop by drop for 1 hour. After that, the mixed solution is stirred for 2 hours at the room temperature, 1 hour at about 50, 30 minutes at about 60 and 2 hours at about 80. After that, the mixed solution is hydrated and cooled to the room temperature, and then a concentrated hydrochloric acid solution is further added to the mixed solution. After the mixed solution is extracted with ethyl acetate (EA) twice, the extracts mixed in an organic layer are sequentially washed with water solution and a saturated saline solution. Then, the extracts are dehydrated with anhydrous magnesium sulfate ($MgSO_4$). After the solvent is evaporated through decompression, column chromatography (silica gel column, methylbenzene) is performed on the residuals to obtain a product 2.

Sodium hydroxide is added to the product 2 and then the mixture is stirred for 1 hour at about 120, wherein the generated acetone is removed by using a pressure evaporator. After that, the product 2 is purified through column chromatography (silica gel column, methylbenzene) to obtain a product 3.

Under nitrogen environment, iodophenol is dissolved in a mixed solution of DMF, triethylamine ($Et_3N$), tetrakistriphenylphosphine palladium ($Pd(PPh_3)_4$) and copper iodide (CuI), and then the mixed solution is heated to about 55. The product 3 is continually added to the mixed solution drop by drop for 20 minutes, and then the mixed solution is stirred for 3 hours. After that, the mixed solution is hydrated and cooled to the room temperature, and then a concentrated hydrochloric acid solution is further added to the mixed solution. After the mixed solution is extracted with ethyl acetate (EA) twice, the extracts mixed in an organic layer are sequentially washed with water solution and a saturated saline solution. Then, the extracts are dehydrated with anhydrous magnesium sulfate ($MgSO_4$). After the solvent is evaporated through decompression, column chromatography (silica gel column, methylbenzene) is performed on the residuals to obtain a product 4.

About 4.14 mmol of product 4 are loaded into a about 250 ml two-neck bottle which is then deaerated with a vacuum dehydrating and deaerating device and nitrogenated for three times. Next, nitrogen is connected to the drip tube for making the reaction system anaerobic and anhydrous. At the room temperature, about 8.28 mmol of triethylamine ($Et_3N$) and about 50 ml of dehydrated THF are added to the reaction system which is then stirred until dissolved. Then, under freezing condition, about 9.11 mmol of methacryloyl chloride are added to the reaction system which reacts until the next day at the room temperature. The reaction system is suction filtrated with THF, and the filtrate is collected, decompressed and evaporated, extracted with EA and water, dehydrated with $MgSO_4$, suction filtrated and evaporated and vacuumed to obtain a yellow solid. Lastly, the yellow solid is purified with EA/hexane=1/6 through silica gel column chromatography to obtain a yellowish solid which can also be crystallized with THF/methanol to obtain a polymerizable monomer of the present embodiment of the present invention, that is, the compound H.

Ninth Embodiment

Each substituent in the chemical formula of the said polymerizable monomer is substituted as follows: m=1, "Z" is an ethynyl, "$X_1$" and "$X_2$" respectively are an oxygen atom, "$Sp_1$" and "$Sp_2$" respectively are an ethyl, "$P_1$" and "$P_2$" respectively are group IV, that is, the compound I. "Y" (that is, "R" in the diagram) of group IV is a hydrogen atom, methyl, fluorine atom, trifluoromethyl, and phenyl.

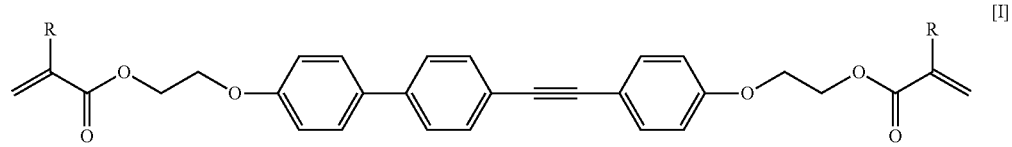

[I]

In the light of structure, the dihedral angle of the hard core structure of the compound I is tiny, and the structure even can be coplanar so as to have better performance in alignment. Besides, the UV light absorption wavelength of the compound I is substantially larger than 300 nm so as to shorten the required radiation time for perfect polymerization. In the present embodiment of the present invention, the synthesis of polymerizable monomer is represented by the following chemical reaction scheme:

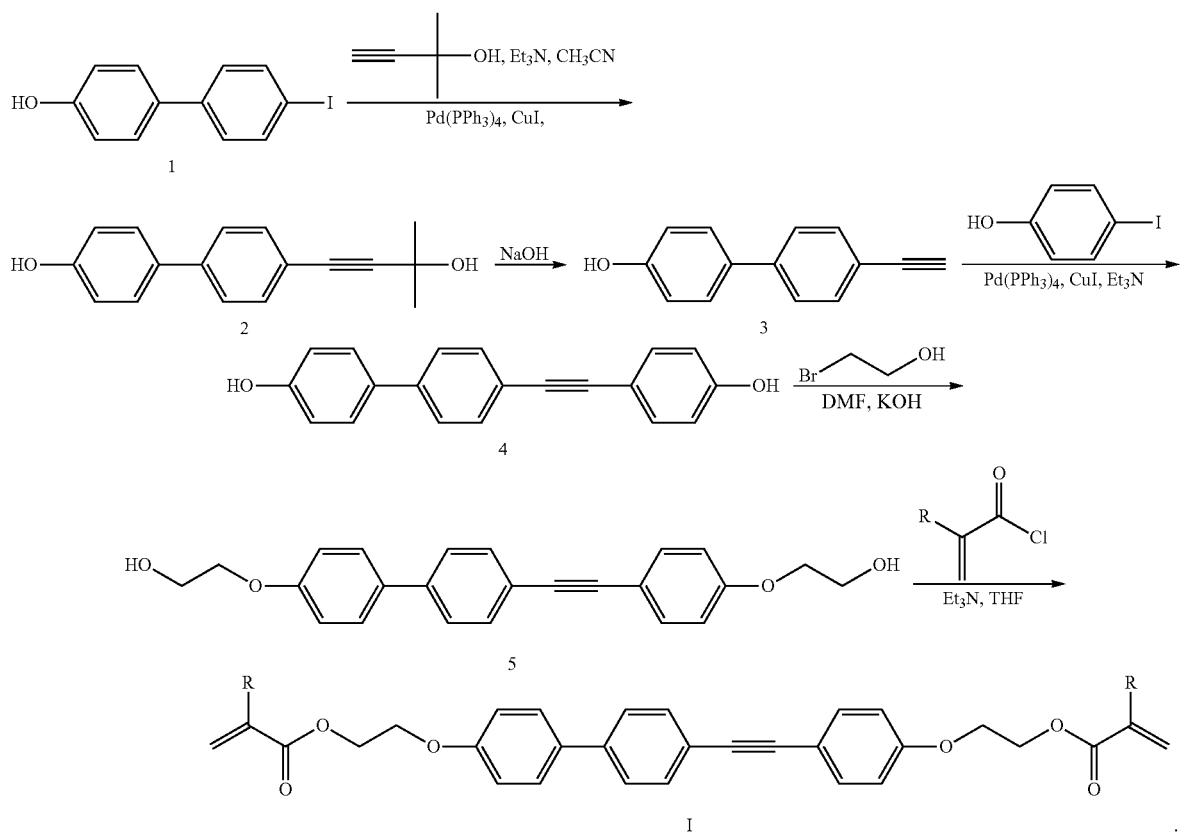

The product 4 is obtained from the reactant 1 the according to the method of the eighth embodiment. Under nitrogen environment, the product 4 is dissolved in a mixed solution of DMF and potassium hydroxide and the mixed solution is then heated to reflow. 2-bromoethenol is continually added to the mixed solution drop by drop for 20 minutes, and then the mixed solution is stirred for 12 hours. Next, the mixed solution is hydrated and cooled to the room temperature, and then a concentrated hydrochloric acid solution is further added to the mixed solution. After the mixed solution is extracted with ethyl acetate (EA) twice, the extracts mixed in an organic layer are sequentially washed with water solution and a saturated saline solution, and then is dehydrated with anhydrous magnesium sulfate ($MgSO_4$). After the solvent is evaporated through decompression, column chromatography (silica gel column, methylbenzene) is performed on the residuals to obtain a product 5.

The product 5 (about 4.14 mmol) is loaded into a about 250 ml two-neck bottle, which is then deaerated with a vacuum dehydrating and deaerating device and nitrogenated for three times. Next, nitrogen is connected to the drip tube for making the reaction system anaerobic and anhydrous. At the room temperature, $Et_3N$ (about 8.28 mmol) and about 50 ml of dehydrated THF are added to the reaction system which is then stirred until dissolved. Then, under freezing condition, mathacryloyl chloride (about 9.11 mmol) is added to the reaction system which reacts until the next day at the room temperature. The reaction system is suction filtrated, decompressed and evaporated, extracted with EA and water, dehydrated with $MgSO_4$, suction filtrated and evaporated and vacuumed to obtain a yellow solid. Lastly, the yellow solid is purified with EA/hexane=1/6 through silica gel column chromatography to obtain a yellowish solid which can also be crystallized with THF/methanol. Lastly, a polymerizable monomer of the present embodiment of the present invention, that is, the compound I, is obtained.

Application of Polymerizable Monomer

The present invention provides a polymerizable monomer adapted to the polymer-stabilizing alignment (PSA) technology which dopes the polymerizable monomer in a liquid crystal material for manufacturing a display panel. When adapted to the PSA technology, various liquid crystal molecules can be added to the polymerizable monomer of the present invention to form different liquid crystal materials. A number of embodiments are disclosed below for detailed descriptions of the composition and ratios of liquid crystal materials. The liquid crystal material provided in the present invention has lower rotational viscosity ($\gamma^1$) and thus has lower drag force during rotation than that of the conventional liquid crystal material. In addition, the liquid crystal material provided in the present invention requires less UV light dose for polymerization than that of the concentional liquid crystal material. Thus, the display panel using the liquid crystal material of the present invention is advantaged with lower manufacturing cost and faster response. One skilled in the art would understand that the polymerizable monomer of the present invention can also be mixed with other liquid crystal molecules to form various liquid crystal materials, and is not limited to the exemplifications of the present invention.

In the present embodiment of the present invention, the liquid crystal material includes many liquid crystal molecules and the said polymerizable monomer. The many liquid crystal molecules include a first liquid crystal molecule, a second liquid crystal molecule and a third liquid crystal molecule. The first liquid crystal molecule is selected from at least one of the compound 1-1 and the compound 1-2 which are respectively represented as the following chemical formulas:

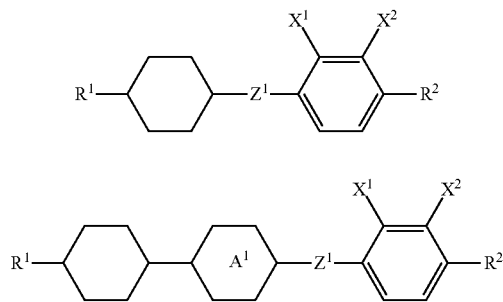

[1-1]

[1-2]

The second liquid crystal molecules is selected from at least one of the compound 2-1 and the compound 2-2 which are respectively represented as the following chemical reaction formulas:

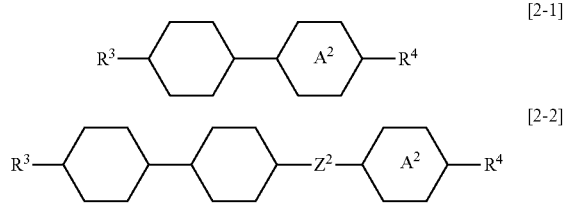

[2-1]

[2-2]

The third liquid crystal molecules is selected from at least one of the compound 3-1 and the compound 3-2 which are respectively represented as the following chemical reaction formulas:

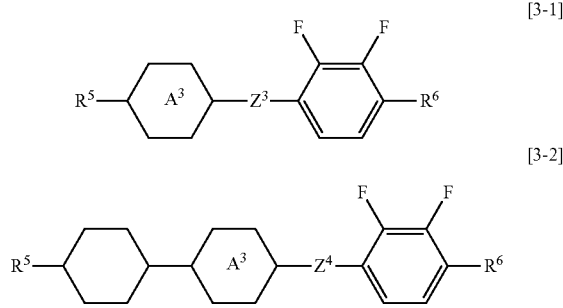

[3-1]

[3-2]

"$R^1$" and "$R^5$" are independently an alkyl with 1~8 carbon atoms or an alkenyl with 2~8 carbon atoms. "$R^2$" and "$R^6$" are independently an alkyl with 1~8 carbon atoms or an alkoxy with 1~7 carbon atoms. "$R^3$" is an alkyl with 1~8 carbon atoms or an alkoxy with 2~8 carbon atoms. "$R^4$" is an alkyl with 1~8 carbon atoms, an alkoxy with 2~8 carbon atoms, or an alkoxy with 1~7 carbon atoms.

"$Z^1$" is a single bond, ethyl ($-C_2H_4-$) or methyoxy ($-CH_2O-$). "$Z^2$" is a single bond, ethyl ($-C_2H_4-$), methyoxy ($-CH_2O-$) or caroboxyl ($-COO-$). "$Z^3$" is a single bond, ethyl ($-C_2H_4-$), difluoromethoxy ($-CF_2O-$), difluoropropoxy ($-OCF_2C_2H_4-$), or ethyl carbonyl ($-C_2H_4COO-$). "$Z^4$" is a single bond, ethyl ($-C_2H_4-$), difluoromethoxy ($-CF_2O-$), or difluoropropoxy ($-OCF_2C_2H_4-$).

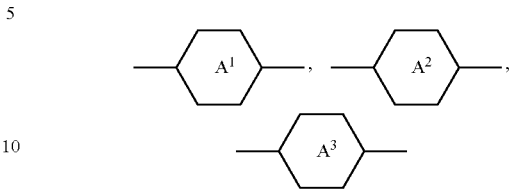

are independently 1,4-cyclohexylene, or 1,4-phenylene.

In "$X^1$" and "$X^2$", one is a fluorine atom, and the other is a chlorine atom.

The three compounds are mixed at the following ratios: the weight of the first compound preferably is about 30% to about 70% of the total weight of the liquid crystal material, the weight of the second compound is about 10% to about 50% of the total weight of the liquid crystal material, and the weight of the third compound is about 20% to about 60% of the total weight of the liquid crystal material. After the liquid crystal materials are uniformly mixed, a polymerizable monomer is added thereto. The doping weight of the polymerizable monomer is about 0.1% to about 10%, preferably about 0.1% to about 0.3%, of the total weight of the above liquid crystal materials. The liquid crystal material with the above composition and ratios can be directly adapted to a display panel.

Referring to FIG. 1, the composition and the ratios of a liquid crystal material according to one preferred embodiment of the present invention are shown. The liquid crystal material of the present embodiment is based on the following composition: about 10.8% is the first compound 1-2, about 21.3% is the second compound 2-1, about 5.8% is the second compound 2-2, about 25.7% is the third compound 3-1 and about 36.4% is the third compound 3-2. Lastly, the compound H (that is, the polymerizable monomer of the eighth embodiment) whose weight is about 0.3% of the total weight of the above liquid crystal material is added. The comparison between the liquid crystal material after mixture and a conventional liquid crystal material is illustrated in FIG. 2. The comparison shows that the two liquid crystal materials are similar in terms of nematic-isotropic phase-transition temperature (Tni), optical anisotropy, and dielectric anisotropy, so the liquid crystal material of the present embodiment of the present invention can be directly adapted to the existing manufacturing process or specifications of display panel. However, the two liquid crystal materials have huge difference in terms of rotational viscosity ($\gamma^1$). The rotational viscosity of the liquid crystal material of the present embodiment of the present invention is merely 67 mPa*s, much lower than that of the conventional liquid crystal material, 90 mPa*s. This implies the drag force of the liquid crystal material of the present embodiment during rotation is small, and thus the response time is reduced.

Besides, when the ratio of liquid crystal molecule changes, the characteristics of the liquid crystal material, such as rotational viscosity and/or nematic-isotropic phase-transition temperature directly affecting the response time and/or operation temperature of a display panel, can be adjusted accordingly. Thus, makers can work out an optimum liquid crystal material according to product designs or customer demands. For example, by reducing the ratio of the second compound and increasing the ratios of the first compound and the third compound, the nematic-isotropic phase-transition temperature of the liquid crystal material can be increased.

The liquid crystal material preferably of the present embodiment of the present invention includes a polymerization initiator whose weight is below about 0.002% of the total weight of the liquid crystal material. The polymerization initiator has strong reactivity, and thus can facilitate the polymerizable monomer distributed over the liquid crystal molecule to start polymerization reaction when energy (such as a heat source or a light source) is provided thereto.

After the mixture of liquid crystal material is completed, the liquid crystal material is disposed between two substrates, and then a voltage is applied to the two substrates for facilitating the arrangement of polymerizable monomer as the liquid crystal molecules rotate. At the same time, an energy source (such as a UV light or a heat source) is applied for facilitating the polymerizable monomers to be polymerized into a polymer film at a particular tilt angle. Even in the absence of voltage, the polymer film still can guide the arrangement of the liquid crystal molecules of a display panel. The manufacturing of display panel is thus completed. The polymerizable monomer of the present invention can be polymerized into polymer with less UV light dose, hence reducing the manufacturing cost.

FIG. 3 shows a side view of a display panel according to a preferred embodiment of the present invention. The display panel 100 using the above liquid crystal material includes an upper substrate 110, a lower substrate 120 and a liquid crystal layer interposed between the two substrates. The liquid crystal layer includes liquid crystal molecules 135 and a polymer film 145. The polymer film 145 is formed by a plurality of polymerizable monomers polymerized on the surface of at least one of the upper substrate 110 or the lower substrate 120 through the PSA technology, and is used for guiding the arrangement of the liquid crystal molecules 135 and generating a pre-tilt angle from the two substrates. Preferably, the average coarseness on the surface of the polymer film 145 approximately ranges between 10 nm to 20 nm. The display panel manufacturing according to the above method has a shorter response time, implying that the polymer film of the display panel has better performance in alignment. The results of a number of experiments are illustrated below.

Test of Response Time of Display Panel:

A number of experiment groups are disclosed below for more detailed descriptions of the composition and the UV light radiation dose of the liquid crystal material. After a display panel is manufactured according to the above composition and radiation dose, the response time of the display panel is tested for the comparison of performance between the conventional material and the liquid crystal material of the present invention.

In all groups, the composition and ratios of liquid crystal molecules of the liquid crystal material are the same. The composition and ratios are as follows: about 10.8% is the first compound 1-2, about 21.3% is the second compound 2-1, about 5.8% is the second compound 2-2, about 25.7% is the third compound 3-1, about 36.4% is the third compound 3-2 and the polymerizable monomer is about 0.3% of the total weight of the liquid crystal material. However, each group has respective polymerizable monomer. Group 1 is a contrast group and includes the conventional monomer; groups 2-3 include the polymerizable monomer of the eighth embodiment, that is, the compound H. Under the same experimental conditions, the liquid crystal material of each group is disposed between two substrates, and then a voltage and a UV light are applied for the polymerizable monomer to be polymerized. A larger UV light radiation dose, that is, 10200 mJ, is applied to groups 1-2, and a lower UV light radiation dose, that is, 7650 mJ, is applied to group 3. The experimental parameters of each group are summarized in Table 1.

TABLE 1

| | Experimental Conditions | | |
|---|---|---|---|
| Group | Liquid Crystal Molecules | Polymerizable Monomer | UV Light Radiation Dose (mJ) |
| 1 | Same | Conventional Monomer | 10200 |
| 2 | Same | Compound H | 10200 |
| 3 | Same | Compound H | 7650 |

Figure 4:
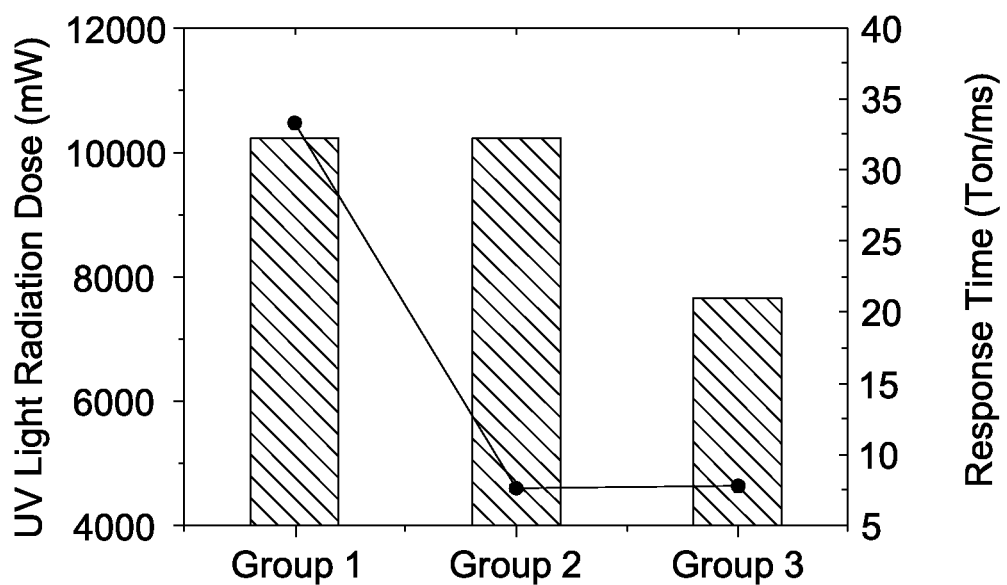
FIG. 4 shows the UV light radiation dose and the response time during the manufacturing process of a conventional display panel and the display panel according to a preferred embodiment of the present invention.

After the display panel is manufactured, response time test is performed on the display panel for each group. Under different driving voltages, the required response time ($T_{on}$) for the liquid crystal compound to be rotated to a predetermined position from an initial position is illustrated in FIG. 4. The coordinate axis at the left-hand side denotes the UV light radiation dose, and the coordinate axis at the right-hand side denotes the response time. The comparison between group 1 (contrast group) and group 2 shows that the UV light radiation dose for both groups is the same, but the response time for group 1 and group 2 are about 33.3 mS and about 7.8 mS, respectively. That is, suppose all the conditions of the manufacturing process remain unchanged for each group, the response rate of the display panel will be increased by about 77% as the monomer of the liquid crystal material is replaced with the polymerizable monomer of the third embodiment of the present invention. Such experimental result shows that the hard core structure of the polymerizable monomer of the present invention has tiny dihedral angle, so the polymerizable monomer has excellent performance in the arrangement and the alignment of liquid crystal molecules and largely increases the response rate of display panel.

Group 2 and group 3 have the same composition of liquid crystal material but are different in the UV light radiation dose, and the comparison between group 2 and group 3 shows that the response time of display panel for group 2 and group 3 are about 7.8 mS and about 7.6 mS, respectively. That is, despite the UV light radiation dose is reduced by about 25%, the manufactured display panel still remain the same response rate. Such experimental result shows that the polymerizable monomer of present invention requires less UV light radiation dose for perfect polymerization than the conventional monomer. As a consequence, the manufacturing time is shorted and energy consumption is reduced.

Accordingly, the polymerizable monomer of the eighth embodiment of the present invention requires less UV light radiation dose for polymerization, and the display panel using the same has shorter response time and faster response rate. Thus, the polymerizable monomer of the eighth embodiment of the present invention not only reduces the manufacturing cost but also increase the response rate of display panel.

The polymerizable monomer, the liquid crystal material and the display panel disclosed in the above embodiments of the present invention have the following advantages:

Firstly, the polymerizable monomer of the present invention requires less UV light radiation dose for polymerization. Despite the UV light dose is reduced by about 25%, the response rate of display panel still remains the same which implies that the required UV light radiation dose can be further reduced, and accordingly, the manufacturing time can be shortened, and the power consumption and the manufacturing cost can also be reduced.

Secondly, the polymerizable monomer has excellent performance in alignment. In the light of structure, the hard core structure of the polymerizable monomer of the present invention has tiny dihedral angle. The experimental result shows that the response rate of the display panel will be increased by about 77% as the monomer of the liquid crystal material is replaced with the polymerizable monomer of the third embodiment of the present invention. Thus, the polymerizable monomer of the present invention has excellent performance in the arrangement and the alignment of liquid crystal molecules and largely increases the response rate of display panel.

Thirdly, the liquid crystal material has small rotational viscosity. The experimental result shows that the liquid crystal material of the preferred embodiment of the present invention has small rotational viscosity which implies the drag force of the liquid crystal material during rotation is small, and thus the response time of the of display panel is reduced.

While the present invention has been described by way of example and in terms of a preferred embodiment, it is to be understood that the present invention is not limited thereto. On the contrary, it is intended to cover various modifications and similar arrangements and procedures, and the scope of the appended claims therefore should be accorded the broadest interpretation so as to encompass all such modifications and similar arrangements and procedures.

What is claimed is:

1. A polymerizable monomer adapted to a display panel, represented by a chemical formula as follows:

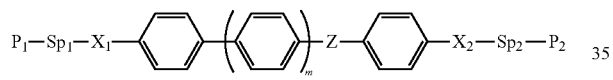

where,
m=0;
"Z" is a caroboxyl group;
"$X_1$" and "$X_2$" are respectively a single bond;
"$Sp_1$" and "$Sp_2$" are respectively a single bond; and
"$P_1$" and "$P_2$" are respectively represented by a group having a chemical formula [IV] as follows:

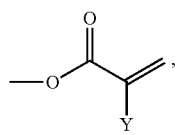
[IV]

where "Y" is selected from fluorine, a trifluoromethyl group, and a phenyl group.

2. A liquid crystal material adapted to a display panel, wherein the liquid crystal material comprises a liquid crystal molecule and the polymerizable monomer of claim 1.

3. The liquid crystal material according to claim 2, wherein the polymerizable monomer has a doping weight that is about 0.1% to about 10% of total weight of the liquid crystal material.

4. The liquid crystal material according to claim 2, wherein the liquid crystal molecule comprises:
a first liquid crystal molecule selected from at least one of a compound 1-1 and a compound 1-2 respectively represented by chemical formulae as follows:

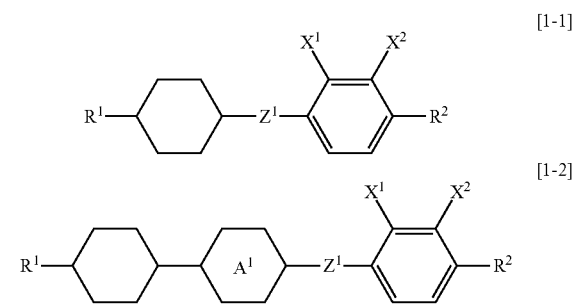

a second liquid crystal molecule selected from at least one of a compound 2-1 and a compound 2-2 respectively represented by chemical formulae as follows:

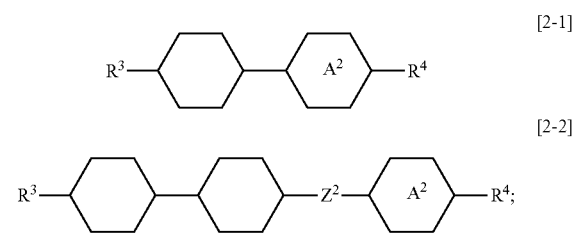

and a third liquid crystal molecule selected from at least one of a compound 3-1 and a compound 3-2 respectively represented by chemical formulae as follows:

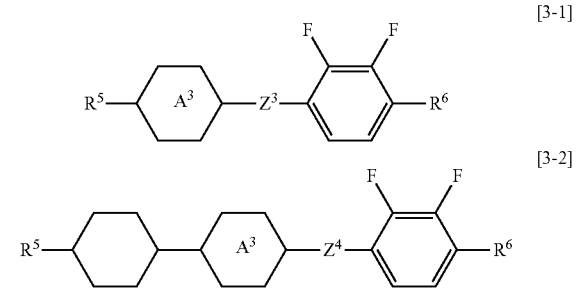

where,
"$R^1$" and "$R^5$" are independently alkyl with 1~8 carbon atoms or alkenyl with 2~8 carbon atoms;
"$R^2$" and "$R^6$" are independently alkyl with 1~8 carbon atoms or alkoxy with 1~7 carbon atoms;
"$R^3$" is alkyl with 1~8 carbon atoms or alkoxy with 2~8 carbon atoms;
"$R^4$" is alkyl with 1~8 carbon atoms, alkoxy with 2~8 carbon atoms or alkoxy with 1~7 carbon atoms;
"$Z^1$" is single bond, ethyl or methyoxy;
"$Z^2$" is single bond, ethyl, methyoxy or caroboxyl;
"$Z^3$" is single bond, ethyl, difluoromethoxy, difluoropropoxy or ethyl carbonyl;
"$Z^4$" is single bond, ethyl, difluoromethoxy or difluoropropoxy;

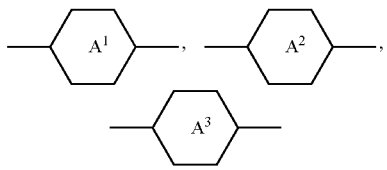

are independently 1,4-cyclohexylene or 1,4-phenylene; and
one of "$X^1$" and "$X^2$" is a fluorine atom, and another of "$X^1$" and "$X^2$" is a chlorine atom.

5. The liquid crystal material according to claim 4, wherein the liquid crystal material contains, based on total weight thereof, from about 30% to about 70% of the first compound, from about 10% to about 50% of the second compound, and from about 20% to about 60% of the third compound.

6. The liquid crystal material according to claim 2, further comprising a polymerization initiator whose weight is below about 0.002% of total weight of the liquid crystal material.

7. A display panel, comprising:
a lower substrate and an upper substrate; and
a liquid crystal layer interposed between the upper substrate and the lower substrate, wherein the liquid crystal layer comprises the liquid crystal material according to claim 2.

8. The display panel according to claim 7, wherein the polymerizable monomers are polymerized into a polymer film whose average surface coarseness ranges from about 10 nm to about 20 nm, and wherein the polymer film is formed either on a surface of the upper substrate or on a surface of the lower substrate, and the polymer film is directly in contact with the liquid crystal layer.

9. A liquid crystal material adapted to a display panel, wherein the liquid crystal material comprises a liquid crystal molecule and a polymerizable monomer, represented by a chemical formula as follows:

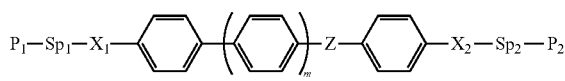

wherein,
m=0;
"Z" is ethynyl;
"$X_1$" and "$X_2$" are respectively an oxygen atom;
"$Sp_1$" and "$Sp_2$" are respectively an ethyl; and
"$P_1$" and "$P_2$" are respectively a group having a chemical formula as follows

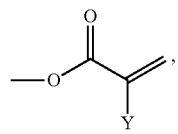

where "Y" is selected from a hydrogen atom, a methyl group, a fluorine atom, a trifluoromethyl group, and a phenyl group;
wherein the liquid crystal molecule comprises:
a first liquid crystal molecule selected from at least one of a compound 1-1 and a compound 1-2 respectively represented by chemical formulae as follows:

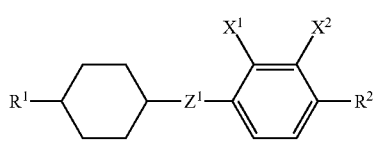

[1-1]

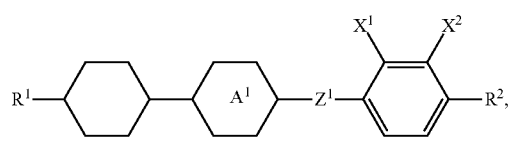

[1-2]

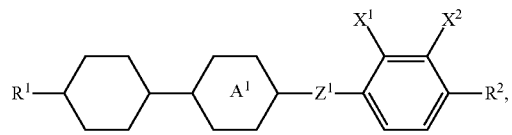

a second liquid crystal molecule selected from at least one of a compound 2-1 and a compound 2-2 respectively represented by chemical formulae as follows:

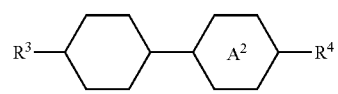

[2-1]

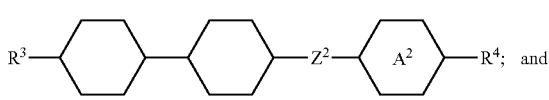

[2-2]

a third liquid crystal molecule selected from at least one of a compound 3-1 and a compound 3-2 respectively represented by chemical formulae as follows:

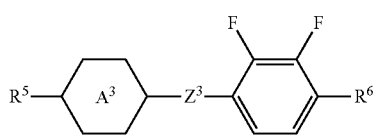

[3-1]

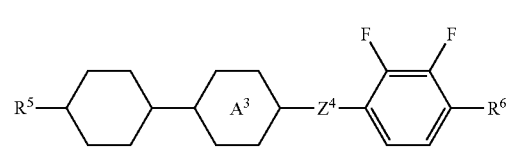

[3-2]

where,
"$R^1$" and "$R^5$" are independently alkyl with 1~8 carbon atoms or alkenyl with 2~8 carbon atoms;
"$R^2$" and "$R^6$" are independently alkyl with 1~8 carbon atoms or alkoxy with 1~7 carbon atoms;
"$R^3$" is alkyl with 1~8 carbon atoms or alkoxy with 2~8 carbon atoms;
"$R^4$" is alkyl with 1~8 carbon atoms, alkoxy with 2~8 carbon atoms or alkoxy with 1~7 carbon atoms;
"$Z^1$" is single bond, ethyl or methyoxy;
"$Z^2$" is single bond, ethyl, methyoxy or caroboxyl;
"$Z^3$" is single bond, ethyl, difluoromethoxy, difluoropropoxy or ethyl carbonyl;
"$Z^4$" is single bond, ethyl, difluoromethoxy or difluoropropoxy;

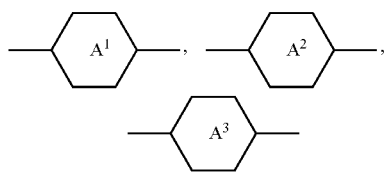

are independently 1,4-cyclohexylene or 1,4-phenylene; and one of "X¹" and "X²" is a fluorine atom, and another of "X¹" and "X²" is a chlorine atom.

10. The liquid crystal material according to claim 9, wherein the polymerizable monomer has a doping weight that is about 0.1% to about 10% of total weight of the liquid crystal material.

11. The liquid crystal material according to claim 9, wherein the liquid crystal material contains, based on total weight thereof, from about 30% to about 70% of the first compound, from about 10% to about 50% of the second compound, and from about 20% to about 60% of the third compound.

12. The liquid crystal material according to claim 9, further comprising a polymerization initiator whose weight is below about 0.002% of total weight of the liquid crystal material.

13. The liquid crystal material according to claim 9, wherein the polymerizable monomers are polymerized into a polymer film whose average surface coarseness ranges about 10 nm to about 20 nm, and wherein the polymer film is formed either on a surface of the upper substrate or on a surface of the lower substrate, and the polymer film is directly in contact with the liquid crystal layer.

\* \* \* \* \*